(12) United States Patent
Yu et al.

(10) Patent No.: US 11,021,656 B2
(45) Date of Patent: Jun. 1, 2021

(54) SYSTEM AND METHOD TO MITIGATE FOULING DURING A HYDROCARBON REFINING PROCESS

(71) Applicant: BL TECHNOLOGIES, INC., Minnetonka, MN (US)

(72) Inventors: Guangzhe Yu, The Woodlands, TX (US); Nimeshkumar Kantilal Patel, The Woodlands, TX (US); Bryan Christopher Crom, The Woodlands, TX (US); Anthony Fields, The Woodlands, TX (US); Roberto Manuel Gutierez, The Woodlands, TX (US); Xiomara Price, The Woodlands, TX (US)

(73) Assignee: BL TECHNOLOGIES, INC., Minnetonka, MN (US)

( * ) Notice: Subject to any disclaimer, the term of this patent is extended or adjusted under 35 U.S.C. 154(b) by 196 days.

(21) Appl. No.: 16/060,172

(22) PCT Filed: Dec. 7, 2016

(86) PCT No.: PCT/US2016/065232
§ 371 (c)(1),
(2) Date: Jun. 7, 2018

(87) PCT Pub. No.: WO2017/100224
PCT Pub. Date: Jun. 15, 2017

(65) Prior Publication Data
US 2018/0362867 A1    Dec. 20, 2018

Related U.S. Application Data

(60) Provisional application No. 62/264,003, filed on Dec. 7, 2015.

(51) Int. Cl.
*C10G 9/16*  (2006.01)
*G01N 33/28*  (2006.01)
(Continued)

(52) U.S. Cl.
CPC ............... *C10G 9/16* (2013.01); *C10G 75/00* (2013.01); *G01N 1/4077* (2013.01);
(Continued)

(58) Field of Classification Search
CPC ........ C10G 9/16; C10G 75/00; G01N 1/4077; G01N 33/2823
See application file for complete search history.

(56) References Cited

U.S. PATENT DOCUMENTS

| | | | |
|---|---|---|---|
| 4,822,475 | A | 4/1989 | McDaniel et al. |
| 5,753,802 | A | 5/1998 | Falkler |

(Continued)

FOREIGN PATENT DOCUMENTS

| | | |
|---|---|---|
| CL | 2015000127 A1 | 5/2015 |
| FR | 2578979 | 9/1986 |

(Continued)

OTHER PUBLICATIONS

Fan, Z., et al. :Investigation of Fouling Mechanisms of a Light Crude Oil Using an Alcor Hot Liquid Process Simulator, Energy Fuels, Oct. 14, 2010, vol. 24, No. 11, pp. 6110-6118.

(Continued)

*Primary Examiner* — Nathaniel J Kolb
(74) *Attorney, Agent, or Firm* — Meunier Carlin & Curfman LLC

(57) ABSTRACT

Described herein are systems and methods for evaluating and mitigating the fouling potential of a given crude oil. The system and methods enable the refiner to rapidly and readily identify the particular mechanisms by which a crude oil may (Continued)

foul, and to select the optimal chemical treatment and/or crude blend to mitigate fouling potential.

15 Claims, 4 Drawing Sheets

(51) Int. Cl.
*C10G 75/00* (2006.01)
*G01N 1/40* (2006.01)
*G05B 17/00* (2006.01)

(52) U.S. Cl.
CPC ..... *G01N 33/2823* (2013.01); *G01N 33/2805* (2013.01); *G01N 33/2876* (2013.01); *G01N 2001/4038* (2013.01); *G01N 2001/4088* (2013.01); *G05B 17/00* (2013.01)

(56) References Cited

U.S. PATENT DOCUMENTS

| | | | |
|---|---|---|---|
| 8,647,415 B1 | 2/2014 | De Haan et al. | |
| 2008/0147365 A1 | 6/2008 | Prasad et al. | |
| 2009/0038995 A1 | 2/2009 | Wright et al. | |
| 2010/0116715 A1* | 5/2010 | Cross | C10G 9/007 208/178 |
| 2014/0275663 A1 | 9/2014 | Brons | |
| 2015/0102224 A1* | 4/2015 | Respini | G01N 15/06 250/341.1 |

FOREIGN PATENT DOCUMENTS

| | | |
|---|---|---|
| WO | 2011113017 | 9/2011 |
| WO | 2014068498 | 5/2014 |
| WO | 2014123736 | 8/2014 |

OTHER PUBLICATIONS

Written Opinion dated Dec. 5, 2019, in related SG application No. 11201803607V, 12 pages.
Communication pursuant to Article 94(3) EPC dated Mar. 27, 2019, issued in related EP application No. 16820059.0, 6 pages.
International Search Report and Written Opinion dated May 23, 2017, from International Application No. PCT/US2016/065232, 32 pages.
Foreign associate correspondence and Office Action [Non-English] dated Jan. 30, 2020, issued in related CL application No. 2018-001490, 32 pages.
Office Action issued for Chilean Application No. 2018-001490, dated Jan. 30, 2020. English Summary included.
Office Action issued for Chilean Application No. 2018-001490, dated Jul. 22, 2020. English Summary included.
Communication Pursuant to Article 94(3) EPC dated Apr. 7, 2020, issued in related EP Application No. 16820059.0, 7 pages.
Communication pursuant to Article 94(3) EPC, in connection to EP Application No. 16 820 059.0, dated Feb. 17, 2021.

* cited by examiner

SYSTEM AND METHOD TO MITIGATE FOULING DURING A HYDROCARBON REFINING PROCESS

FIELD OF THE INVENTION

The present invention includes methods of analyzing hydrocarbon samples, including methods of analyzing hydrocarbon samples to predict fouling potential. The present invention provides a method for rapidly and easily determining fouling potential, and thereby improves refining efficiency by identifying optimal hydrocarbon streams and/or chemical treatments for refining processes.

BACKGROUND OF THE INVENTION

The majority of hydrocarbons found on earth naturally occur in crude oil, where decomposed organic matter provides an abundance of carbon and hydrogen which, when bonded, can catenate to form seemingly limitless chains. Hydrocarbons can be refined to produce products such as gasoline, diesel fuel, paraffin wax, and the like. The refining process can include a tank-farm, a cold preheat train, a desalter, a hot preheat train, a crude heater/furnace, a crude distillation unit, a vacuum unit furnace, a vacuum distillation unit, and downstream processing units such a hydrotreater, a hydrocracker, fluid catalytic cracking (FCC), a visbreaker, a coker, etc.

Fouling is generally understood to be the deposition and accumulation of a phase separate from the mobile phase in a refining operation. Unwanted materials such as scale, algae, suspended solids, and insoluble salts can deposit on the surfaces of processing equipment such as boilers and heat exchange.

Crude preheat train fouling decreases refining efficiency, both by requiring additional energy inputs to overcome temperature reduction and interrupting normal refinery operation for cleaning and other maintenance. Fouling is a poorly understood process, the mechanisms by which any particular hydrocarbon stream may foul can differ depending on the particular characteristics of the hydrocarbon. Chemical reactions, corrosion, deposit of existing insoluble impurities in the stream, and deposit of materials rendered insoluble by the temperature difference between the process stream and the heat exchanger wall are all pathways through which fouling can occur. Various chemical treatments are available to reduce fouling, however, there is no universal treatment that will mitigate all fouling mechanisms. Furthermore, it is inefficient to subject a hydrocarbon to all possible chemical treatments, given that many treatments would be unnecessary. As such, a means to predict propensity to fouling, and to determine which chemical treatments would mitigate such fouling, would enable more efficient operation of a refinery.

Methods for evaluating the fouling potential of a hydrocarbon sample have been explored. Generally, these methods rely on analysis of the liquid hydrocarbon itself. However, these methods are typically time consuming, do not evaluate all fouling mechanisms, and are not always reliable.

There remains a strong need for a method that enables refiners to reliably and rapidly predict potential fouling of a given hydrocarbon. There remains a need for robust method would allow refiners to select a hydrocarbon with less fouling potential, as well as to treat a hydrocarbon with the appropriate chemical treatment to minimize fouling.

BRIEF DESCRIPTION

Disclosed herein are systems and methods of rapidly and easily evaluating the fouling potential of a given hydrocarbon composition.

In one aspect, a method of analyzing a hydrocarbon composition during a refining process is described. This method comprises analyzing a hydrocarbon sample, wherein the hydrocarbon sample is representative of an amount of the hydrocarbon composition entering a refining process; and then selecting the appropriate optimization step to minimize fouling. The optimization can include one or more chemical treatments, optimizing the ratio of hydrocarbon blends, and combinations thereof.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

DRAWINGS

The accompanying drawings, which are incorporated in and constitute a part of this specification, illustrate embodiments and together with the description, serve to explain the principles of the methods and systems:

DETAILED DESCRIPTION

Figure 1:
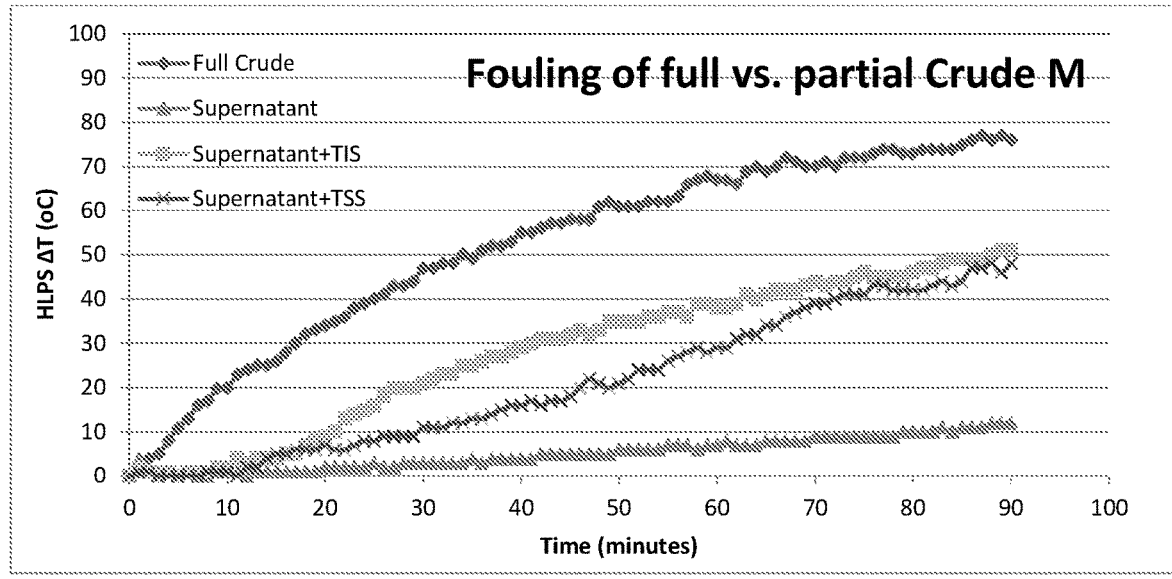
FIG. 1 depicts $\Delta T$ analysis of a hydrocarbon sample (diamond data points), a hydrocarbon supernatant (triangle data points), a hydrocarbon sample with toluene-soluble solids removed (square data points), and a hydrocarbon sample with toluene insoluble solids removed (x data points).

Before the present methods and systems are disclosed and described, it is to be understood that the methods and systems are not limited to specific methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

As used herein, the term "fouling" refers to the accumulation of a phase separate from the mobile phase on the surfaces of refinery equipment. For instance, non-gaseous material can separate from a gaseous mobile phase and non-liquid material can separate from a liquid mobile phase. The separated phase reduces the space through which the hydrocarbon can pass, and reduces the contact between the hydrocarbon and heat exchanger surfaces.

As used herein, the term "hydrocarbon composition" or "hydrocarbon sample" refers to crude oil, crude oil blends, tower bottoms, gas oil, naphtha, condensates, slop oil, hydrotreated oil, hydrocracked oil, and mixtures thereof.

Provided herein are methods to evaluate the fouling potential of a given hydrocarbon sample. With detailed understanding of fouling potential in hand, a refiner can take steps to mitigate the fouling. Because the methods disclosed herein provide a previously unavailable level of detail regarding specific fouling mechanisms, the refiner can readily select the appropriate mitigation steps to maximize the efficiency of the refining process. Fouling potential of a crude oil or a blend is defined as its tendency to deposit materials on heat transfer surface, leading to decrease in heat transfer efficiency. Heat exchanger network systems are used to recover as much sensible heat as possible from process streams around the crude distillation unit (CDU) by preheating the feedstock prior to entering the furnace. The more the heat transferred to the feed in the exchangers, the less energy/fuel is required to heat the crude to the required distillation temperature range. The hottest exchangers have a direct impact on the furnace inlet temperature. Exchangers with the highest heat flux or low flow velocity usually show the highest fouling rates. Fouling is caused by the precipitation of materials, both organic and inorganic, present in the feed or formed in the heating process of the crude preheat system. As the heat duty loss is directly proportional to the normalized furnace inlet temperature (NFIT) decline, compensating for the decline in NFIT requires increased fuel in the furnace, and this consequently contributes to an increase in $CO_2$ emissions. By tracking the CDU furnace fuel demand, $CO_2$ emissions can also be quantified. To assist Refiners to optimize crude blends and minimize the fouling potential in crude preheat exchangers and crude furnaces, a more proactive and predictive approach to estimate fouling potential is a significant industry need. The fouling potential can be expressed in more than one way, such as the loss of heat transfer (delta T, or $\Delta T$), increase of pressure drop (delta P, or $\Delta P$) or amount of foulant (e.g., thickness of solids, volume of foulant, or weight of foulant), since all three can reflect the amount of fouling occurring on solid surfaces in a refinery.

In certain selected embodiments, the fouling potential is evaluated by measuring and/or analyzing a hydrocarbon sample and/or various portions thereof. Among the portions that can evaluated include a first portion, which is generally the liquid hydrocarbon and solids dissolved therein, and a second portion, which is generally dispersed solids, gels, colloids, salts and other compounds suspended in the hydrocarbon sample. The second portion can include both solvent soluble and solvent-insoluble components.

In certain embodiments, the fouling potential can be evaluated comparing the first and second portions of the hydrocarbon. In certain selected embodiments, the hydrocarbon composition is separated into at least a first portion and a second portion. The fouling potential can be determined by measuring and/or comparing the first and second portions. Measuring can include steps such as determining the concentration, volume, and/or mass of the first and/or second portion in the hydrocarbon sample, and the comparing can include comparing the volume and/or mass of the first portion and the second portion relative to one another and/or to the hydrocarbon sample. In some selected embodiments, the fouling potential can be determined without separating the first and second portions, using methods for detecting and measuring total solid content, or total inorganic/organic content. Suitable methods include, but are not limited to microscopy, UV-vis spectroscopy, light scattering, and acoustic resonance. In certain embodiments, combinations of the above methods can be employed. In some embodiments, the fouling potential is based on the amount of solids and/or inorganic and/or organic content in either the hydrocarbon sample, and/or in one or more of a variety of portions into which the hydrocarbon sample can be divided. In the present application, the term "hydrocarbon sample" is the initial hydrocarbon sample prior to separation resulting in the first, second, third, and/or fourth portions.

The fouling potential can also be determined by separating the second portion into at least a third portion and a fourth portion wherein the third portion includes the components of the second portion that are soluble in a solvent, and the fourth composition includes the components of the second portion that insoluble in that solvent. The third and fourth portions can be measured, for instance, to obtain the volume and/or mass of the third and fourth portions which can be compared with each other and/or with the volume and/or mass of the first portion and/or hydrocarbon sample. In some embodiments, the fouling potential can be determined by conducting some or all of the above steps.

The hydrocarbon sample can be separated into the first and second portions using techniques suitable for separating dispersed solids from a liquid. In certain selected embodiments, the first and second portions can be separated by filtration, electrophoresis, centrifugation, field-flow fractionation, cyclonic separation, gravimetric separation and combinations thereof. In certain selected embodiments, the hydrocarbon is separated at ambient temperature, while in other embodiments, the hydrocarbon is separated at elevated temperature. The separation at elevated temperature can be accomplished by first heating the hydrocarbon before subjecting it to the separation step, or the separation at elevated temperature can be accomplished by heating the hydrocarbon while subjecting it to the separation step.

In certain embodiments, the separation step can include a centrifugation. The centrifugation can be carried out at ambient temperature or above, for instance, >30° C., >40° C., >50° C., >60° C., >70° C., >80° C., >90° C., or >100° C. In some embodiments, the centrifugation can be carried out at 30-100° C., 40-100° C., 50-100° C., 60-100° C., 60-90° C., or 70-90° C. The centrifugation can be carried out at >500 rpm, >600 rpm, >700 rpm, >800 rpm, >1,000 rpm, >1,200 rpm, >1,400 rpm, >1,600 rpm, >1,800 rpm, or >2,000 rpm. In some embodiments, the centrifugation can be carried out at 1,000-2,000 rpm, 1,200-2,000 rpm, 1,400-2,000 rpm, or 1,400-1,800 rpm. The centrifugation can be carried out for >5 minutes, >10 minutes, >15 minutes, >20 minutes, >25 minutes, >30 minutes, >35 minutes, >40 minutes, >45 minutes, >50 minutes, >55 minutes, or >60 minutes. In some embodiments, the centrifugation can be carried out for 5-60 minutes, 15-60 minutes, 5-45 minutes, or 15-45 minutes. The supernatant can be separated from the collected solids to give the first and second portions.

The second portion can be separated into a third and fourth portion by extraction with one or more polar or nonpolar solvents, dispersants, acids, bases, or combinations thereof. In certain selected embodiments, the solvent is a non-polar solvent such as an aromatic hydrocarbon solvent. Exemplary aromatic hydrocarbon solvents include, but are not limited to, benzene, aromatic naphtha and alkyl benzenes such as toluene, ethylbenzene, and xylenes (unless specified otherwise, the term "xylenes" includes all three positional isomers, either as single isomer or a mixture of two or more isomers). The extraction solvent can be a mixture of two or more of the foregoing solvents. In some selected embodiments, the extraction step can include washing with aqueous acid to dissolve inorganic solids, leaving organic solids behind. Exemplary aqueous acids include mineral acids such as sulfuric acid, phosphoric acid, nitric acid, hydrochloric acid, hydrobromic acid, hydrofluoric acid and hydroiodic acid, organic acids such as sulfonic acids like methanesulfonic acid and toluenesulfonic acid, or carboxylic acids such as trifluoroacetic acid. In some selected embodiments, the extraction step can include washing with an aqueous base. Exemplary bases include LiOH, NaOH, KOH, $Ca(OH)_2$, $Mg(OH)_2$, $NH_4OH$, $K_2CO_3$, $Na_2CO_3$ and combinations thereof. In some selected embodiments, the second portion can be separated by washing with dispersants, such as solutions of one or more of alkyl sulfonates, alkyl phenate sulfide, alkyl phosphorous sulfide, alkylphenols, alkylphenol sulfide, alkyl phosphate phenate sulfide, polyalkylene succinimide, polyalkylene thiophosphonic acid ester, alkyl succinic esters, and combinations thereof.

In certain selected embodiments, the fouling potential can be determined by analyzing the hydrocarbon composition, the first portion, the second portion, the third portion, and/or the fourth portion. The analysis can be conducted by directly (experimentally) determining the individual contents of the hydrocarbon sample such as any chemical composition analysis including liquid chromatography, density and/or viscosity measurement, etc. Dynamic or kinematic viscosity can be measured at temperatures ranging from 0 to 500° C., with a shear rate from 0.01 to 100,000 $s^{-1}$. In some selected embodiments, the analysis can be performed using one or more of fingerprinting, thermogravimetric analysis, and/or inductively coupled plasma mass spectroscopy. The portions can be heated or distilled during or prior to the analysis. Suitable fingerprinting analysis includes spectroscopy, for instance infrared spectroscopy, near-infrared spectroscopy, and nuclear magnetic resonance spectroscopy.

The fingerprint analysis can be performed using infrared spectroscopy, for instance as described in U.S. Pat. No. 6,087,662, the disclosure of which is hereby incorporated by reference. For instance, the fingerprint analysis can be used to measure asphaltene concentration using multiple variable regression analysis, specifically, by:

measuring at least one frequency in the middle infrared absorption in the band of 3800-700 $cm^{-1}$.

taking each of the absorbances measured, or a mathematical function thereof;

performing statistical treatment using the above absorbances or functions as individual independent variables;

assigning and applying weighting constants or their equivalents to said independent variables;

applying the above steps using compositions of known asphaltenes concentration to calibrate the instrument and determine said weighting constants or equivalents;

repeating said steps with unknown compositions, and applying the weighting constants or equivalents determined during said calibration with compositions of known asphaltenes concentration to output a signal or signals indicative of asphaltenes concentration for the unknown compositions.

In some embodiments, the fouling potential is based on a combination of A) the amount of solids and/or inorganic and/or organic content in either the hydrocarbon sample, and/or in one or more of a variety of portions into which the hydrocarbon sample can be divided, such as the first, second, third, and/or fourth portions obtained as mentioned above and B) additional analysis conducted on the hydrocarbon sample and/or the first, second, third, and/or fourth portions mentioned above.

The determination of A) the amount of solids and/or inorganic and/or organic content mentioned above, can be done by measuring and/or comparing the first and second portions. Measuring can include steps such as determining the concentration, volume, and/or mass of the first and/or second portion in the hydrocarbon sample, and the comparing can include comparing the volume and/or mass of the first portion and the second portion relative to one another. In some selected embodiments. A) can be determined without separating the first and second portions, using methods for detecting and measuring total solid content, or total inorganic/organic content. Suitable methods include, but are not limited to microscopy, UV-vis spectroscopy, light scattering, and acoustic resonance. In certain embodiments, combinations of the above methods can be employed. In some embodiments, A) is based on the amount of solids and/or inorganic and/or organic content in either the hydrocarbon sample, and/or in one or more of a variety of portions into which the hydrocarbon sample can be divided.

The determination of A) the amount of solids and/or inorganic and/or organic content mentioned above can be done by separating the second portion into at least a third portion and a fourth portion wherein the third portion includes the components of the second portion that are soluble in a solvent, and the fourth composition includes the components of the second portion that insoluble in that solvent. The third and fourth portions can be measured, for instance, to obtain the volume and/or mass of the third and fourth portions which can be compared with each other and/or with the volume and/or mass of the first portion and/or hydrocarbon sample. In some embodiments, A) can be determined by conducting some or all of the above steps.

The determination of B) can done by analyzing the hydrocarbon composition, the first portion, the second portion, the third portion, and/or the fourth portion. The analysis can be conducted by directly (experimentally) determining the individual contents of the hydrocarbon sample such as any chemical composition analysis including liquid chromatography, density and/or viscosity measurement, etc. Dynamic or kinematic viscosity can be measured at temperatures ranging from 0 to 500° C., with a shear rate from 0.01 to 100,000 $s^{-1}$. In some selected embodiments, the analysis can be performed using one or more of fingerprinting, thermogravimetric analysis, and/or inductively coupled plasma mass spectroscopy. The portions can be heated or distilled during or prior to the analysis. Suitable fingerprinting analysis includes spectroscopy, for instance infrared spectroscopy, near-infrared spectroscopy, and nuclear magnetic resonance spectroscopy.

In some embodiments, the fouling potential may be characterized using $\Delta T$, i.e., the loss of heat transfer as measured in a Hot Liquid Process Simulator. The method is a derivative of ASTM D3241 "Thermal Oxidation Stability of Aviation Fuels" (JFTOT method), and is widely used by hydrocarbon refiners and servicers. Higher $\Delta T$ values indicate a greater propensity of fouling. In other embodiments, the fouling potential may be measured using the Hot Ribbon Test, disclosed, for instance, in U.S. Pat. No. 5,614,081. The Hot Ribbon Test measures the amount of residue deposited ($W_{dep}$) on a heated surface that is in contact with a hydrocarbon sample. Higher $W_{dep}$ values indicate a greater propensity for fouling.

In at least certain selected embodiments, average fouling propensity, e.g., $\Delta T_{ave}$ can be estimated according to Predictive Formula 1:

$$\Delta T_{ave} = a \cdot [TIS]^b \cdot \mu^c \cdot Res^d + f \cdot [TSS]^g \cdot \mu^h \cdot Res^i$$

where a~i∈[−1000,1000]. In certain embodiments:
a is from −500 to 500, or −1000 to 0, or 0 to 200, or 200 to 1000;
b is from −10000 to 0, or −5000 to 5000, or 1 to 1000, or 0 to 10000;
c is from 0 to 10, or 10 to 200, or −50 to 50;
d is from 0 to 10, or 10 to 200, or −50 to 50;
e is from −500 to 500, or −1000 to 0, or 0 to 200, or 200 to 1000;
f is from 0 to 10, or 10 to 200, or −50 to 50;
g is from 0 to 10, or 10 to 200, or −50 to 50;
h is from 0 to 10, or 10 to 200, or −50 to 50.

$\Delta T_{ave}$ is the average loss of heat transfer in 90 minutes on the HLPS, [TIS] (toluene insoluble solids) is the percent fraction (by volume) of portion 4 relative to the hydrocarbon sample when using toluene as the extraction solvent, [TSS] (toluene soluble solids) is the percent fraction (by volume) of portion 3 relative to the hydrocarbon sample when using toluene as the extraction solvent, $\mu$ is the viscosity from either direct measurement or fingerprinting analysis of the hydrocarbon sample, [Res] is the percent concentration of resins in the hydrocarbon sample either from measurement or from fingerprint. In some embodiments, $\Delta T_{ave}$ can incorporate both A) (the amount of solids and/or inorganic and/or organic content) and B) (additional analysis conducted on the hydrocarbon sample and/or the first, second, third, and/or fourth portions) mentioned above, such as A) including the determination of [TIS] and [TSS], and B) including the determination of other properties such as viscosity and [Res].

In some selected embodiments, $\Delta T_{ave}$ can be estimated according to Predictive Formula 2:

$$\Delta T_{ave} = a + b \cdot [TIS] + c \cdot [TCS] + d \cdot [RIX] \cdot [TCS] + e \cdot [TCS]^f + g \cdot RIX^h + i \cdot Res + j \cdot Asp + k \cdot RIX^l \cdot Res + m \cdot RIX^n \cdot Asp$$

where a~n∈[−1000,1000]. In certain embodiments;
a is from 0 to 10, or 10 to 200, or −100 to 100;
b is from −500 to 500, or −1000 to 0, or 0 to 500, or 200 to 1000;
c is from 0 to 10, or 10 to 200, or −100 to 100;
d is from 0 to 10, or 10 to 200, or −100 to 100;
e is from −500 to 500, or −1000 to 0, or 0 to 500, or 200 to 1000;
f is from 0 to 10, or 10 to 200, or −100 to 100;
g is from 0 to 10, or 10 to 200, or −100 to 100;
h is from 0 to 10, or 10 to 200, or −100 to 100;
i is from 0 to 10, or 10 to 200, or −100 to 100;
j is from 0 to 10, or 10 to 200, or −100 to 100;
k is from 0 to 10, or 10 to 200, or −100 to 100;
l is from 0 to 10, or 10 to 200, or −100 to 100;
m is from 0 to 10, or 10 to 200, or −100 to 100;
n is from 0 to 10, or 10 to 200, or −100 to 100.

[TIS], [TSS] are as defined above, RIX is the relative instability number from the fingerprint of the hydrocarbon sample, [TCS] (aka., total centrifuged solids) is the percent fraction (by volume) of portion 2 relative to the hydrocarbon sample, and [Asp] is the percent concentration of asphaltenes either from measurement or the fingerprint of the hydrocarbon sample. In some embodiments, $\Delta T_{ave}$ associated with Predictive Formula 2 can incorporate both A) (the amount of solids and/or inorganic and/or organic content) and B) (additional analysis conducted on the hydrocarbon sample and/or the first, second, third, and/or fourth portions) mentioned above, such as A) including the determination of [TIS] and [TSS], and, including the determination of other properties such as viscosity, [Res], RIX, and [Asp].

The relative amounts of the first, second, third and/or fourth portions can inform the specific mitigation steps that a refiner should take to reduce fouling.

After analysis of a hydrocarbon, the refiner can select the appropriate blending and/or chemical treatment to mitigate fouling potential. The HLPS test includes a heated test section in a heat exchanger, where a tested fluid is electrically heated. The outlet fluid is the fluid that exits the from the heated test section. The maximum temperature of the outlet fluid is the maximum temperature measured at the exit of the heated test section in a specific period of the HLPS test. In certain selected embodiments, temperature of the outlet fluid at the heated test section of the HLPS is subtracted from the maximum temperature of the outlet fluid during the run to obtain $\Delta T$ before treatment, which is a measure of fouling since the temperature of the outlet fluid can vary depending on fouling. The fouling is mitigated such that the average ΔT in the initial 90 minutes is less than about 75° C., after treatment the average ΔT in the initial 90 minutes is less than about 75° C., 50° C., 45° C., 40° C., 35° C., 30° C., 25° C., 20° C., or 15° C. as measured by the HLPS method. In some selected embodiments, preference is given for fouling mitigation such that $\Delta T_{ave}$ after 90 minutes is less than about 50° C., while in other selected embodiment fouling mitigation is such that $\Delta T_{ave}$ after 90 minutes is less than about 25° C.

The chemical treatment can be applied during production, transportation, storage, processing, and/or distribution of the hydrocarbon composition. The chemical treatment can include one or more one or more wetting agents, emulsion breakers, detergents, dispersants, stabilizers, corrosion inhibitors, sulphide or metal-sulphide dissolvers, polymerization inhibitors, antioxidants and metal deactivators or combinations thereof.

Fouling potential can be reduced by blending two or more separate hydrocarbon samples. A refiner which primary employs a high-fouling hydrocarbon crude can blend one or more low-fouling hydrocarbon crudes with the high-fouling crude to give a blend with overall reduced fouling potential. The low-fouling crude can be blended at a ratio of 1%, 2.5%, 5%, 10%, 15%, 20% or 25% by volume or weight, or at a ratio of from 1-25%, 5-25%, 10-25% or 10-20% by volume or weight.

The methods of determining fouling potential described above can be performed either on or offline during a refining process. In an offline measurement, fouling potential of hydrocarbon samples could be measured on a separated sample from the hydrocarbon stream with devices separated from the refinery units, and then mitigation steps taken on the hydrocarbon stream. For instance, hydrocarbon streams can be treated with an appropriate chemical treatment, or blended prior to entering the refining process. In an online process, streams can be measured with or without a sample being withdrawn, for instance, the pre-heat train or crude furnace. In an online process, one or more measurements can be taken in real-time and automatically and/or one or more predictions can be made in real-time and automatically and/or one or more processes can be controlled in real-time and automatically according to the measurement(s) and/or prediction(s). Based on the fouling potential obtained, the refiner can add mitigation chemicals to the processing tanks, pipelines, desalters and the like. Mitigations chemical can be added to multiple components as well. In some selected embodiments, the refiner can adjust the flow rate, order of blending, and/or introduction or removal of one or more hydrocarbon streams, of the individual crudes entering the refining stream.

In some embodiments, the presence of a high amount of nonpolar solvent (for instance, toluene) insoluble solids can suggest that acids, bases, metal deactivators, free radical scavengers, and/or antioxidants will successfully mitigate fouling. In some embodiments, the presence of a high amount of solvent soluble solids can suggest that asphaltene dispersants will successfully mitigate fouling. In comparison with previous methods in which each class of chemical treatment may have been separately evaluated, the instantly disclosed methods enable the refiner to rapidly identify the optimal chemical treatment regimen.

In certain selected embodiments, the individual fouling propensity can be determined for two or more hydrocarbon compositions, and the streams can then be combined in a ratio in which the combined streams have lower fouling propensity than either of the individual streams. In certain selected embodiments, the fouling potential of a high-fouling crude (for instance, a crude with $\Delta T_{ave}$ after 90 minutes greater than about 50° C., 60° C., 75° C., or 90° C.) can be mitigated by determining the fouling potential of a number of different low-fouling hydrocarbon compositions (for instance, a crude with $\Delta T_{ave}$ after 90 minutes less than about 15° C., 10° C., 5° C., 2.5° C.), and then selecting the low-fouling composition that, upon blending, will best mitigate the fouling of the high-fouling crude.

The solutions presented in the present application can be conducted with a time lag, or they can be conducted dynamically, which is essentially in real-time with the use of appropriate computer processors.

Example 1

A sample of crude oil was centrifuged at 60-90° C. for 15-45 minutes at 1,400-1,800 rpm. The supernatant was removed to give solids in an amount of 1.7% by weight of the crude oil. The solids were combined with toluene and mixed for 10-20 minutes at 60-90° C. The mixture was centrifuged at 60-90° C. for 15-45 minutes at 1,400-1,800 rpm. The toluene solution was removed to give the toluene insoluble solids (0.2% by weight of the crude oil), and the toluene solvent was removed by distillation to give the toluene soluble solids (1.5% by weight of the crude oil, determined by the difference of total solids and toluene insoluble solids).

A Hot Liquid Process Simulator (HLPS) was used to evaluate the fouling potential of the crude oil, supernatant, supernatant re-combined with toluene soluble solids, and supernatant re-combined with toluene insoluble solids. As depicted in FIG. 1, the crude oil produced a higher ΔT than the supernatant, demonstrating the effect of solids on crude-oil fouling. FIG. 1 also demonstrates how both toluene soluble and toluene insoluble solids contribute to fouling. FIG. 1 depicts ΔT analysis of the hydrocarbon sample (diamond data points), the hydrocarbon supernatant (triangle data points), the hydrocarbon sample with toluene-soluble solids removed (square data points), and the hydrocarbon sample with toluene insoluble solids removed (x data points).

Figure 2:
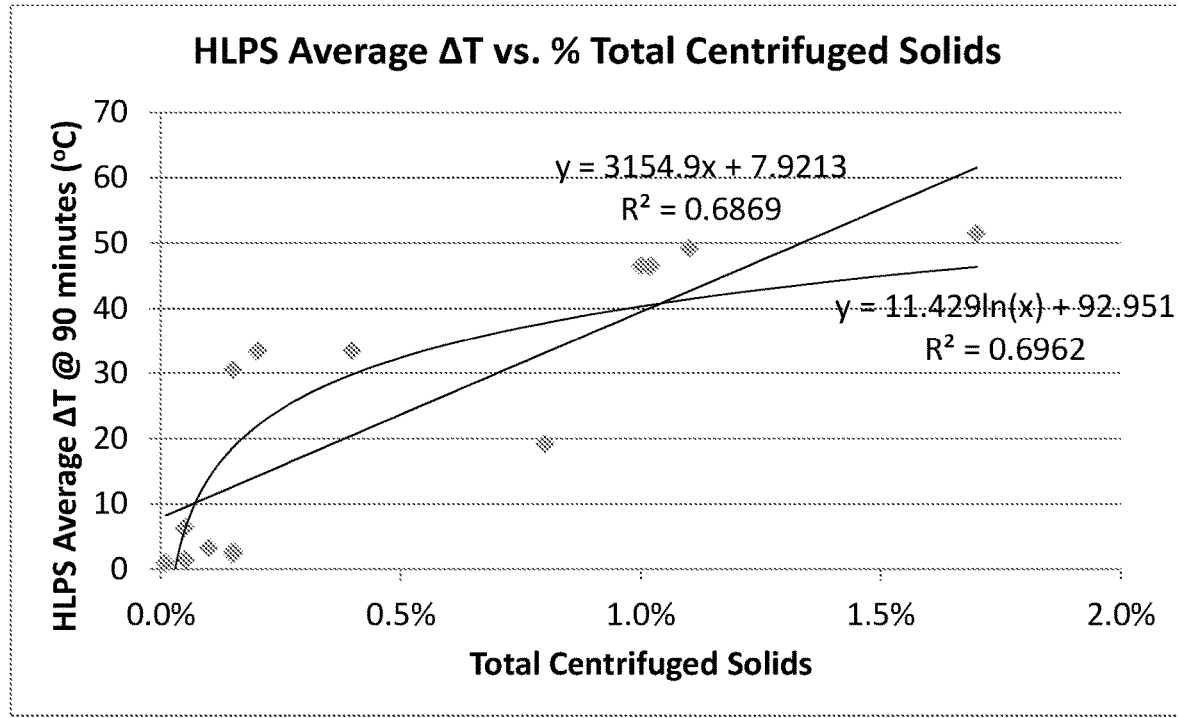
FIG. 2 depicts $\Delta T$ analysis of hydrocarbon samples having differing amounts of total solids.
Figure 3:
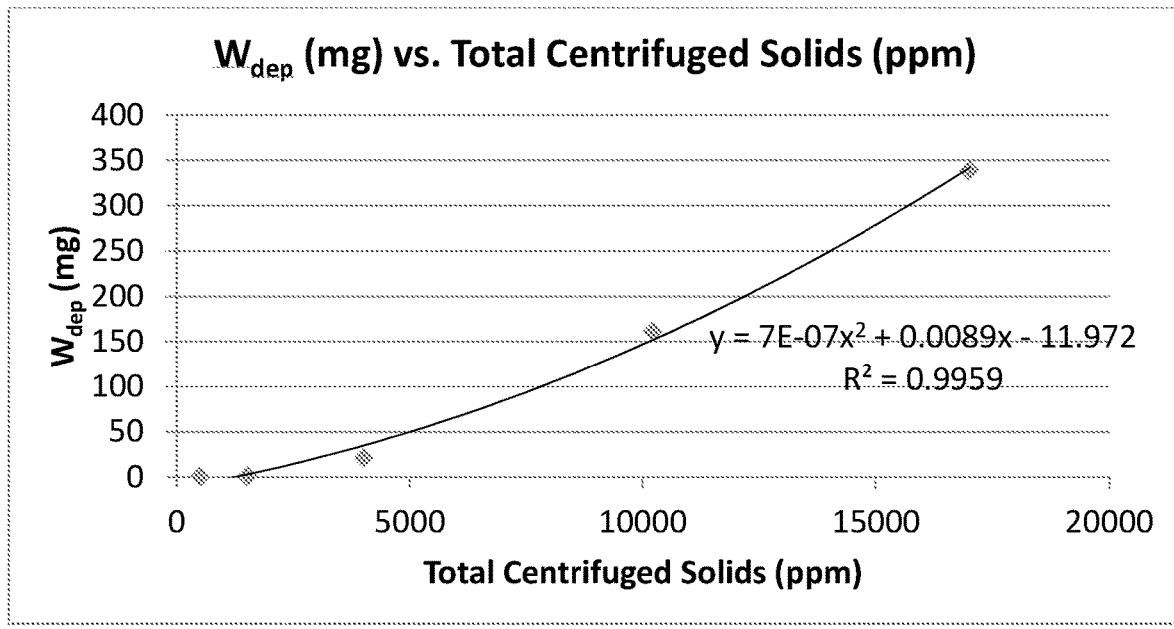
FIG. 3 depicts $W_{dep}$ analysis of hydrocarbon samples having differing amounts of total solids.

FIGS. 2 and 3 both demonstrate that total solids content (evaluated as in Example 1 above) correlate with fouling propensity.

Example 2

Figure 4:
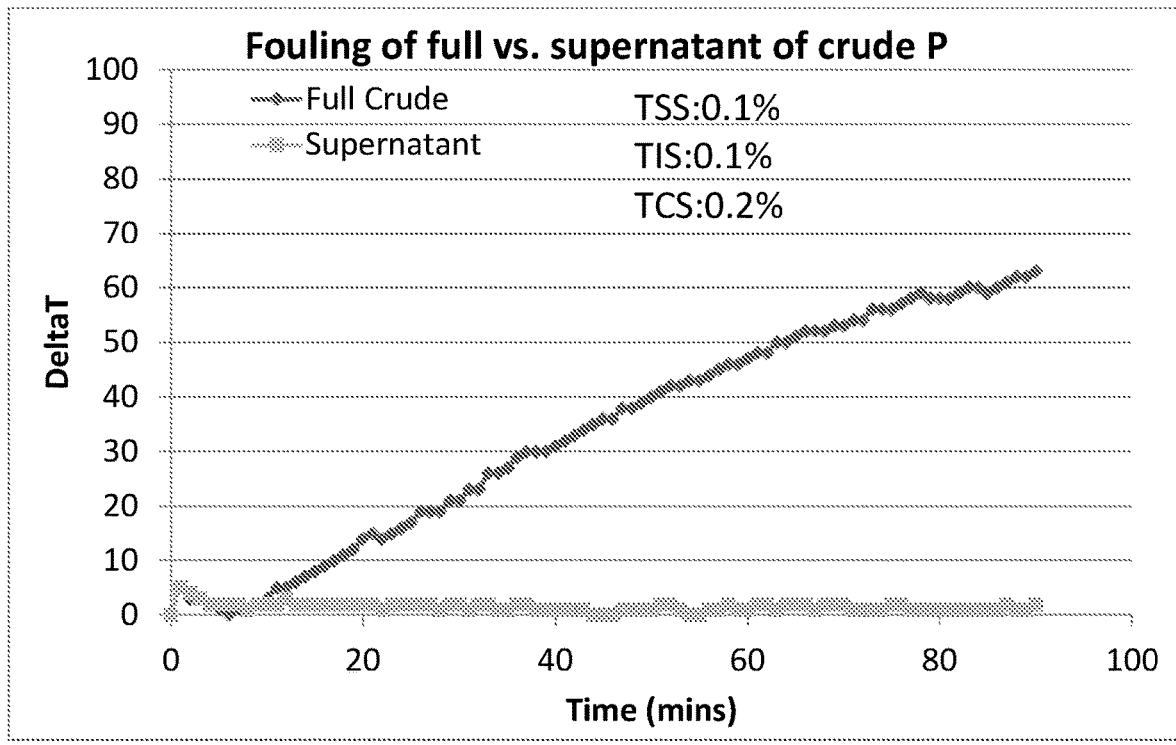
FIG. 4 depicts $\Delta T$ analysis of a crude hydrocarbon sample (diamond data points) and the supernatant of the hydrocarbon sample (square data points).

A sample of a crude oil was centrifuged at 60° C. FIG. 4 depicts the ΔT of the supernatant (obtained by centrifugation at 60° C. (diamond data point)) and crude oil (x data points).

Example 3

Figure 5:
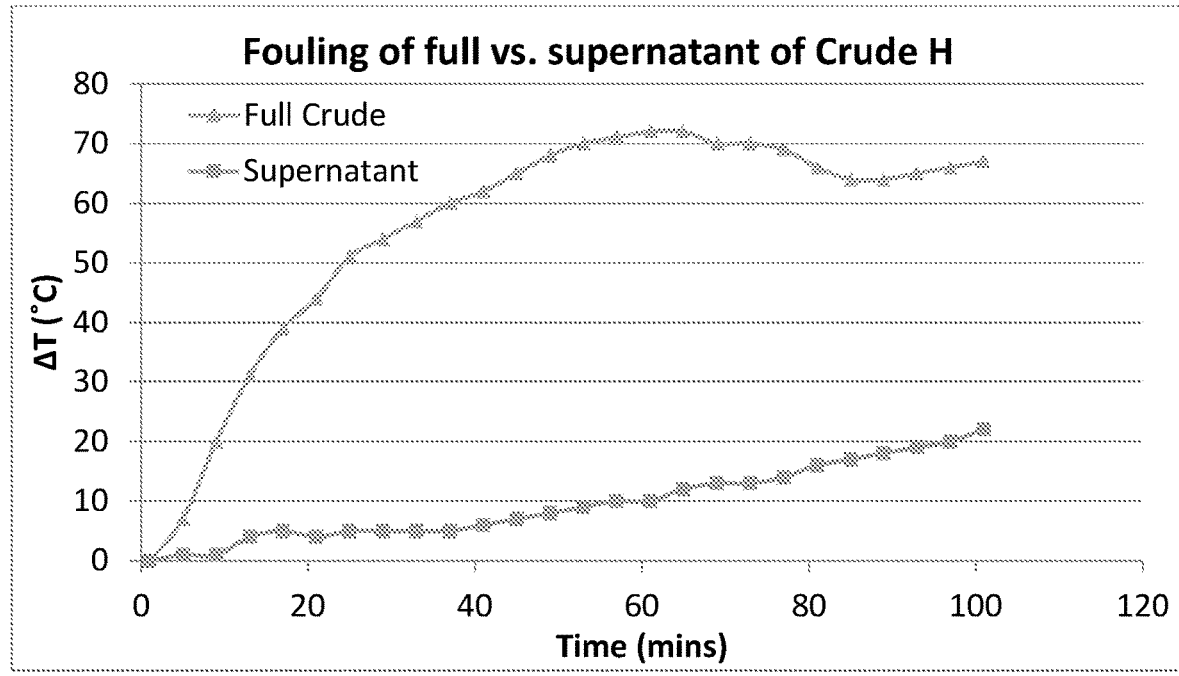
FIG. 5 depicts $\Delta T$ analysis of a crude hydrocarbon sample (triangle data points) and the supernatant obtained by centrifuging at 60° C. (square data points).
Figure 6:
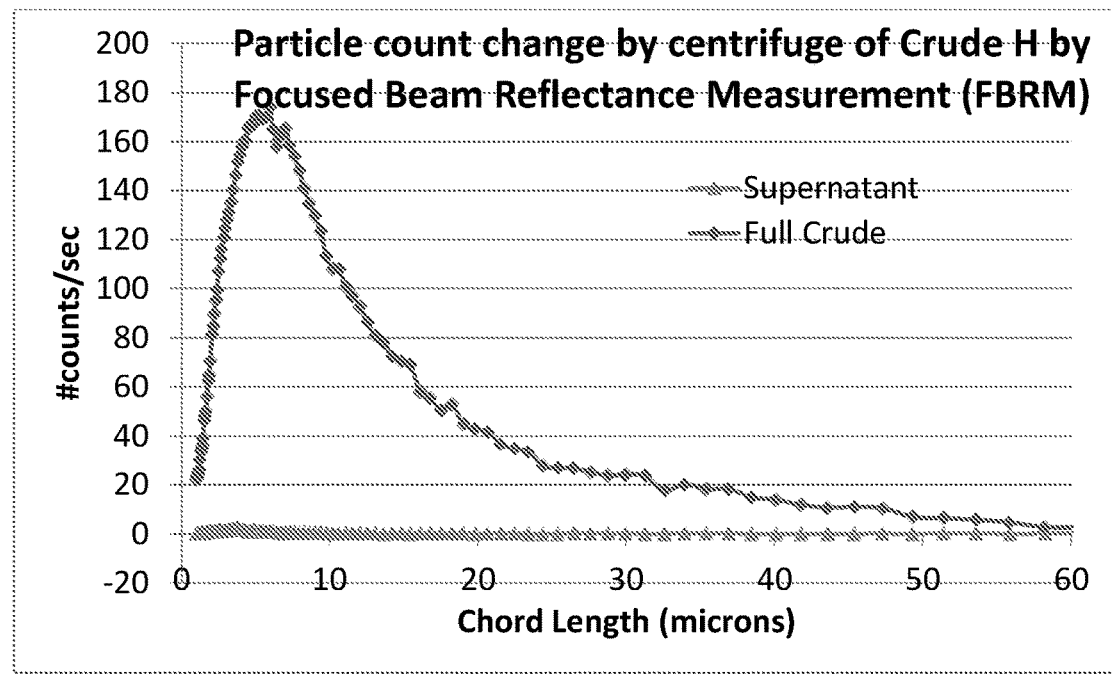
FIG. 6 depicts an analysis of solids content of a crude hydrocarbon sample (diamond data points) and the supernatant obtained by centrifuging at 60° C. (triangle data points).

Samples of crude oil were centrifuged at 60° C. FIG. 5 depicts ΔT of the supernatant (square data point), and the crude oil (triangle data points). FIG. 6 depicts the effect of centrifugation on the solids present in the supernatant, and centrifugation efficiency against micrometer solids. On the X-axis, FIG. 6 shows the chord length of solid particles in the sample, and on the Y-axis it shows the number of counts/sec of such solid particles. FIG. 6 basically shows the centrifugation efficiency against micrometer sized solids since one of the lines is of the full crude and the other of the supernatant obtained after centrifugation.

Example 4

The fouling potential of thirteen different crude oils was measured using infrared fingerprinting, centrifugation and extraction with toluene solvent. Table 1 depicts the data obtained from the measurements.

TABLE 1

| | | Predicted from the Fingerprint | | | | | Measured | | |
|---|---|---|---|---|---|---|---|---|---|
| Crude | RIX | API Gravity | Viscosity (cP) | Saturates (wt %) | Aromatics (wt %) | Resins (wt %) | Asphaltenes (wt %) | Total Centrifuged Solids, TCS (vol %) | Toluene Insoluble Solids, TIS (vol %) | Toluene Soluble Solids, TSS (vol %) |
| I | 7.2 | 45.8 | 7.8 | 89.8 | 7.5 | 1.4 | 1.4 | 0.25 | 0.05 | 0.2 |
| II | 5.2 | 43.3 | 5.8 | 74.3 | 19.1 | 4.4 | 2.2 | 0.04 | 0.005 | 0.035 |
| III | 6.3 | 35.1 | 2.0 | 89.8 | 9.0 | 0.5 | 0.8 | 0.03 | 0.02 | 0.01 |
| IV | 2.9 | 36.1 | 11.2 | 63.7 | 23.4 | 8.4 | 4.5 | 0.175 | 0.05 | 0.125 |
| V | 1.4 | 30.2 | 21.1 | 53.1 | 26.9 | 12.6 | 7.4 | 0.01 | 0 | 0.01 |
| VI | 1.7 | 24.9 | 22.9 | 60.6 | 21.0 | 11.2 | 7.2 | 0.01 | 0 | 0.01 |
| VII | 7.8 | 44.0 | 9.6 | 95.5 | 2.5 | 0.8 | 1.2 | 1 | 0.02 | 0.98 |
| VIII | 4.6 | 40.6 | 9.4 | 79.8 | 13.9 | 3.8 | 2.5 | 1.5 | 0.2 | 1.3 |
| IX | 1.2 | 30.0 | 23.8 | 58.3 | 24.3 | 10.9 | 6.5 | 0.1 | 0.07 | 0.03 |
| X | 1.3 | 31.6 | 18.7 | 54.3 | 27.6 | 11.4 | 6.6 | 0.05 | 0.03 | 0.02 |
| XI | 6.7 | 40.8 | 5.3 | 89.4 | 7.3 | 1.8 | 1.5 | 0.4 | 0.05 | 0.35 |
| XII | 1.4 | 28.8 | 15.7 | 56.9 | 25.3 | 11.6 | 6.2 | 0.025 | 0.02 | 0.005 |
| XIII | 7.4 | 39.1 | 2.0 | 85.9 | 10.3 | 2.4 | 1.4 | 0.1 | 0.02 | 0.08 |

Table 2 depicts the observed vs. calculated fouling rates for the above samples as determined by the two fouling equations.

TABLE 2

| | HLPS Average ΔT@90 minutes (° C.) | | |
|---|---|---|---|
| Crude | Measured | Predictive Model-1 | Predictive Model-2 |
| I | 30.7 | 23.5 | 30.7 |
| II | 14.1 | 11.7 | 14.1 |
| III | 4.8 | 9.0 | 4.8 |
| IV | 8.4 | 17.0 | 8.4 |
| V | 0.1 | 3.4 | 0.3 |
| VI | 1.0 | 3.3 | 0.8 |
| VII | 46.4 | 47.0 | 46.4 |
| VIII | 51.6 | 59.9 | 51.6 |
| IX | 6.4 | 5.7 | 6.3 |
| X | 1.5 | 5.2 | 1.7 |
| XI | 33.5 | 38.4 | 33.5 |
| XII | 3.5 | 2.8 | 1.6 |
| XIII | 30.9 | 28.9 | 28.8 |

Figure 7:
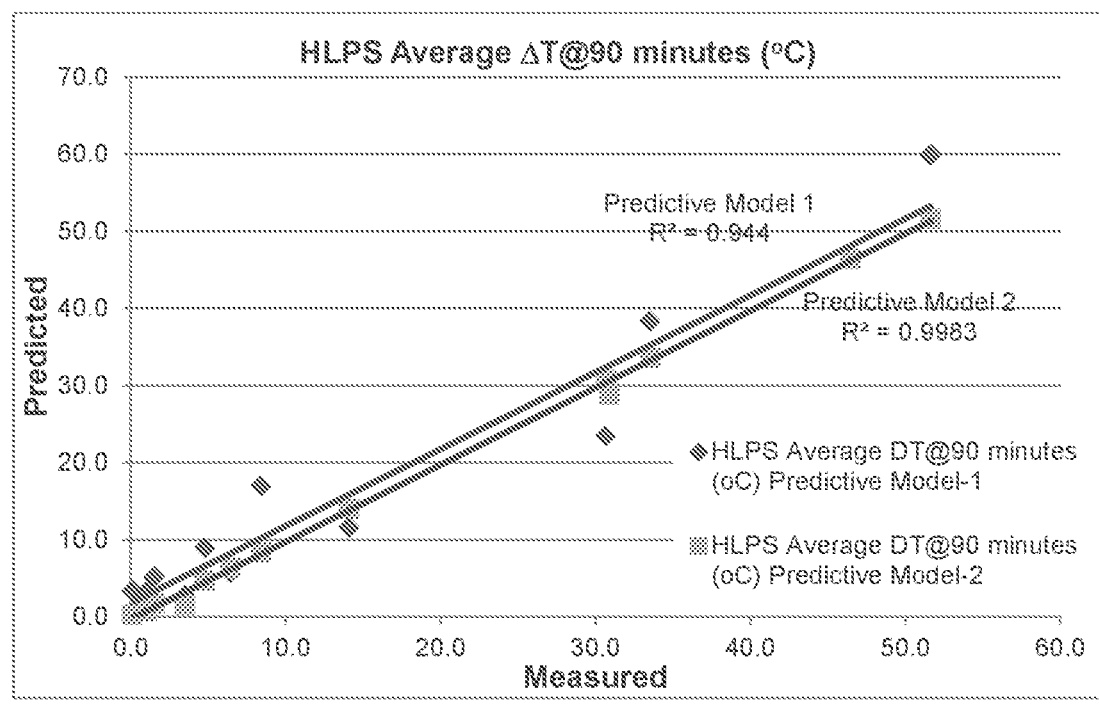
FIG. 7 depicts a comparison of $\Delta T$ measured both experimentally and predicted according the formulae disclosed herein for thirteen different crude samples. The diamond data points were obtained using Predictive Formula 1, and the square data points were obtained using Predictive Formula 2.

Predictive Model-1: $\Delta T_{ave} = \{-140.2 \cdot [TIS]^{379.4} + 142.8 \cdot [TSS]^{0.52}\} \cdot \mu^{-0.48} \cdot Res^{0.053}$
Predictive Model-2: $\Delta T_{ave} = 144.0 \, [TIS] + 6.5 \cdot RIX \cdot [TCS] + 0.39 \cdot [TCS]^{-0.5} + 0.71 \cdot RIX^2 + (6.3 - 0.92 \cdot RIX^2) \cdot (Res + Asp) - 5.1 - 20.2 \cdot [TCS]$ The data presented in Table 2 is graphically depicted in FIG. 7.

Example 5

A refiner that currently processes a high fouling stream (VIII, ΔT90=59.9° C.), can evaluate how to reduce overall fouling by blending low-fouling streams. In particular, the refiner can determine which of 3 low fouling crudes (V, VI and XII) to buy and blend at a 20% volume ratio with the existing stream in order to obtain the lowest fouling in the final blend (Table 3). Predictive Model-1 predicts that VI will give the lowest fouling when blended with crude VIII at a 20% to 80% ratio.

TABLE 3

| Crude | HLPS Average ΔT@90 minutes (° C.) Predictive Model-1 |
|---|---|
| VIII | 59.9 |
| V | 3.4 |

TABLE 3-continued

| Crude | HLPS Average ΔT@90 minutes (° C.) Predictive Model-1 |
|---|---|
| VI | 3.3 |
| XII | 2.8 |
| 80% VIII + 20% III | 50.6 |
| 80% VIII + 20% VI | 40.0 |
| 80% VIII + 20% XII | 42.6 |

Predictive Model-1: $\Delta T_{ave} = a \cdot [TIS]^b \cdot \mu^c \cdot Res^d + f \cdot [TSS]^g \cdot \mu^h \cdot Res^i$
where $a\sim i \in [-1000, 1000]$ Example 6

A refiner can determine the best chemical treatment to treat a high-fouling crude (XI). The crude can be treated with dispersants 1, 2, or 3 and then total centrifuged solids and centrifuged then analyzed for fouling potential. Using these inputs, Predictive Model 1 predicts that dispersant 2 would be the best dispersant which lowers the ΔT90 to 18.8° C. The refiner can make a quick decision on which chemical treatment to use based on the prediction results.

TABLE 4

| Crude | TCS (%) | HLPS Average ΔT@90 minutes (° C.) Predictive Model-1 |
|---|---|---|
| XI | 0.4 | 38.4 |
| XI + 2000 ppm Dispersant 1 | 0.25 | 23.2 |
| XI + 2000 ppm Dispersant 2 | 0.2 | 18.8 |
| XI + 2000 ppm Dispersant 3 | 0.25 | 23.2 |

Predictive Model-1: $\Delta T_{ave} = a \cdot [TIS]^b \cdot \mu^c \cdot Res^d + f \cdot [TSS]^g \cdot \mu^h \cdot Res^i$
where $a\sim i \in [-1000, 1000]$ Dispersant 1 is a polymeric dispersant, dispersant 2 is alkyl phosphorous sulfide dispersant, and dispersant 3 is an alkyl succinic disperant.

The methods and systems of the appended claims are not limited in scope by the specific methods and compositions described herein, which are intended as illustrations of a few aspects of the claims and any methods and systems that are functionally equivalent are within the scope of this disclosure. Various modifications of the methods and systems in addition to those shown and described herein are intended to fall within the scope of the appended claims. Further, while only certain representative methods, systems, and aspects of these methods and systems are specifically described, other methods and systems and combinations of various features of the methods and systems are intended to fall within the scope of the appended claims, even if not specifically recited. Thus a combination of steps, elements, components, or constituents can be explicitly mentioned herein, however, all other combinations of steps, elements, components, and constituents are included, even though not explicitly stated.

The invention claimed is:

1. A method of determining fouling potential of a hydrocarbon composition comprising:
   obtaining a sample of the hydrocarbon composition, said sample comprising saturated hydrocarbons, aromatic hydrocarbons, dispersed solids, resins, and asphaltenes;
   separating the hydrocarbon sample into the first portion comprising liquid hydrocarbons and solids dissolved therein, and the second portion comprising the dispersed solids;
   determining the concentration of the dispersed solids in the hydrocarbon sample;
   separating the second portion into at least a third portion and a fourth portion wherein the third portion comprises a solvent-soluble or solvent-dispersible fraction, and the fourth composition comprises a solvent-insoluble or solvent-undispersable fraction;
   determining the concentration of the solvent-insoluble or solvent-undispersable fraction in the solvent-soluble or solvent-dispersible fraction;
   determining the concentration of saturated hydrocarbons, aromatic hydrocarbons, resins, and asphaltenes in the hydrocarbon composition; and
   determining the fouling potential by comparing the concentrations of the total dispersed solids, the solvent-soluble or solvent-dispersible fraction, the solvent-insoluble or solvent-undispersable fraction, saturated hydrocarbons, aromatic hydrocarbons, dispersed solids, resins, and asphaltenes.

2. The method according to claim 1, wherein the separating of the hydrocarbon composition into the first portion and the second portion comprises filtration, electrophoresis, centrifugation, field-flow fractionation, cyclonic separation, gravimetric separation or a combination thereof.

3. The method according to claim 2, wherein the separation comprises heating.

4. The method according to claim 1, wherein the second portion is separated into at least the third and the fourth portions by extraction with one or more solvents, dispersants, acids, bases, or combinations thereof.

5. The method according to claim 4, wherein the solvent comprises an aromatic hydrocarbon solvent selected from benzene, aromatic naphta, alkylbenzene, or a mixture thereof.

6. The method of claim 5, wherein the alkylbenzene comprises toluene, ethylbenzene, xylenes, or a mixture thereof.

7. The method according to claim 1, wherein the concentration of the saturated hydrocarbons, aromatic hydrocarbons, resins, and asphaltenes is determined by spectroscopically analyzing the hydrocarbon sample, the first portion, or a combination thereof.

8. A system for using predictive analytics in control of a hydrocarbon refining process comprising:
   a memory, wherein the memory stores computer-readable instructions; and
   a processor communicatively coupled with the memory, wherein the processor executes the computer-readable instructions stored on the memory, the computer-readable instructions causing the processor to:
   receive an analysis of a hydrocarbon sample,
   develop one or more predictive models of the hydrocarbon refining process for the hydrocarbon entering the refining process based on the analysis of the crude oil; and
   control aspects of the hydrocarbon refining process as the hydrocarbon entering the refining process moves through the refining process based on the one or more predictive models,
   wherein the analysis is obtained by the following steps:
   obtaining a sample of the hydrocarbon composition, said sample comprising saturated hydrocarbons, aromatic hydrocarbons, dispersed solids, resins, and asphaltenes;
   separating the hydrocarbon sample into the first portion comprising liquid hydrocarbons and solids dissolved therein, and the second portion comprising the dispersed solids;
   determining the concentration of the dispersed solids in the hydrocarbon sample;
   separating the second portion into at least a third portion and a fourth portion wherein the third portion comprises a solvent-soluble or solvent-dispersible fraction, and the fourth composition comprises a solvent-insoluble or solvent-undispersable fraction;
   determining the concentration of the solvent-insoluble or solvent-undispersable fraction in the solvent-soluble or solvent-dispersible fraction;
   determining the concentration of saturated hydrocarbons, aromatic hydrocarbons, resins, and asphaltenes in the hydrocarbon composition; and
   determining the fouling potential by comparing the concentrations of the total dispersed solids, the solvent-soluble or solvent-dispersible fraction, the solvent-insoluble or solvent-undispersable fraction, saturated hydrocarbons, aromatic hydrocarbons, dispersed solids, resins, and asphaltenes.

9. The system according to claim 8, wherein the separating of the hydrocarbon composition into the first portion and the second portion comprises filtration, electrophoresis, centrifugation, field-flow fractionation, cyclonic separation, gravimetric separation or a combination thereof.

10. The system according to claim 9, wherein the separation comprises heating.

11. The system according to claim 8, wherein the second portion is separated into at least the third and the fourth portions by extraction with one or more polar or nonpolar solvents, dispersants, acids, bases, or combinations thereof.

12. The system according to claim 11, wherein the solvent comprises an aromatic hydrocarbon solvent.

13. The system according to claim 12, wherein the solvent comprises an aromatic hydrocarbon solvent selected from benzene, aromatic naphtha, alkylbenzene, or a mixture thereof.

14. The system according to claim 13, wherein the alkylbenzene comprises toluene, ethylbenzene, xylenes, or a mixture thereof.

15. The system according to claim 8, wherein developing one or more predictive models of the hydrocarbon refining process for the hydrocarbon entering the refining process based on the analysis of the hydrocarbon sample comprises developing one or more predictive models based on the analysis that estimate or predict one or more of density, viscosity, total acid number (TAN), percent saturates, percent asphaltenes, percent resins, percent aromatics, asphaltene stability, crude stabilizer (CS) dosage demand, emulsion stability and demulsifier (EB) dosage demand, fouling potential and antifoulant (AF) dosage demand, and corrosion related performance and corrosion inhibitor dosage demand during the hydrocarbon refining process.

* * * * *